United States Patent

Minson

Patent Number: 5,938,591
Date of Patent: Aug. 17, 1999

[54] SELF RETAINING LARYNGOSCOPE

[76] Inventor: Matthew Alan Minson, 1530 Sul Ross #1, Houston, Tex. 77006

[21] Appl. No.: 09/093,621

[22] Filed: Jun. 9, 1998

[51] Int. Cl.$^6$ .................................................... A61B 1/26
[52] U.S. Cl. ......................... 600/191; 600/196; 600/197; 600/199
[58] Field of Search .................................. 600/185, 190, 600/191, 196, 197, 199, 219, 222, 223

[56] References Cited

U.S. PATENT DOCUMENTS 3,716,047  2/1973  Moore et al. ...................... 600/222 X

FOREIGN PATENT DOCUMENTS 2272632  12/1975  France .................................. 600/190

OTHER PUBLICATIONS

Ring, Wallace H., M.D., "A New Device for Exposure of the Oropharynx", Arch Otolaryng, vol. 96 (600/196) Jul. 1972.

*Primary Examiner*—Jeffrey A. Smith
*Attorney, Agent, or Firm*—Arthur M. Dula

[57] ABSTRACT

The invention is a self-retaining disposable laryngoscope having dual light conductive blades that open and lock apart laterally and/or radially. The invention has two curved blades: a tongue blade and a palate blade. These two blades may be separated and locked apart by a ratchet mechanism in the instrument's handle while they remain parallel. This provides a bite block, pushes down the tongue, and makes the invention self-retaining in the airway. The palate blade may be rotated about an axis in the handle of the instrument and locked in position by a ratchet mechanism to spread the distal ends of the blades. This lifts the palate and epiglottis and opens the airway.

10 Claims, 6 Drawing Sheets

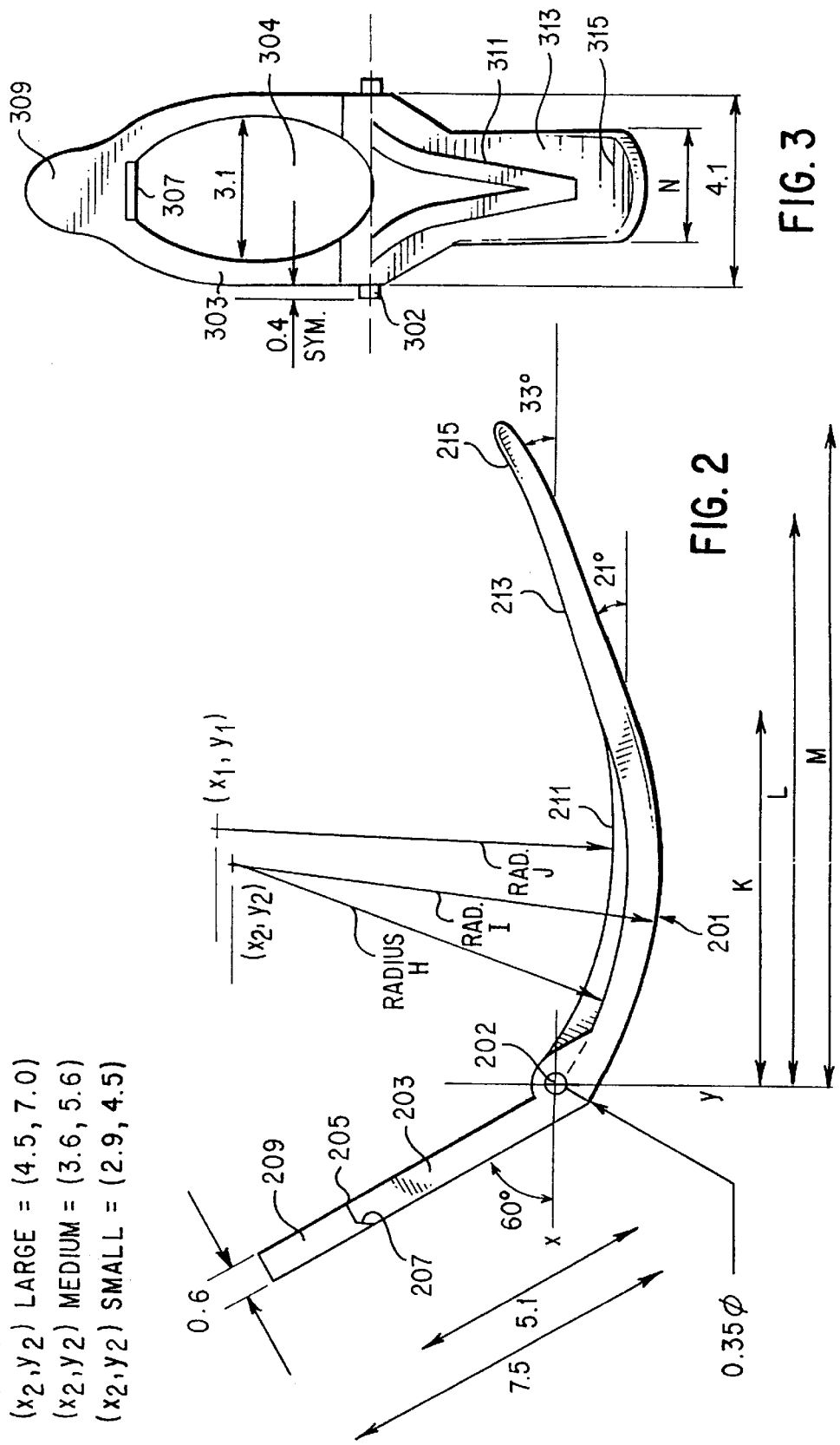

SECT. 7-7

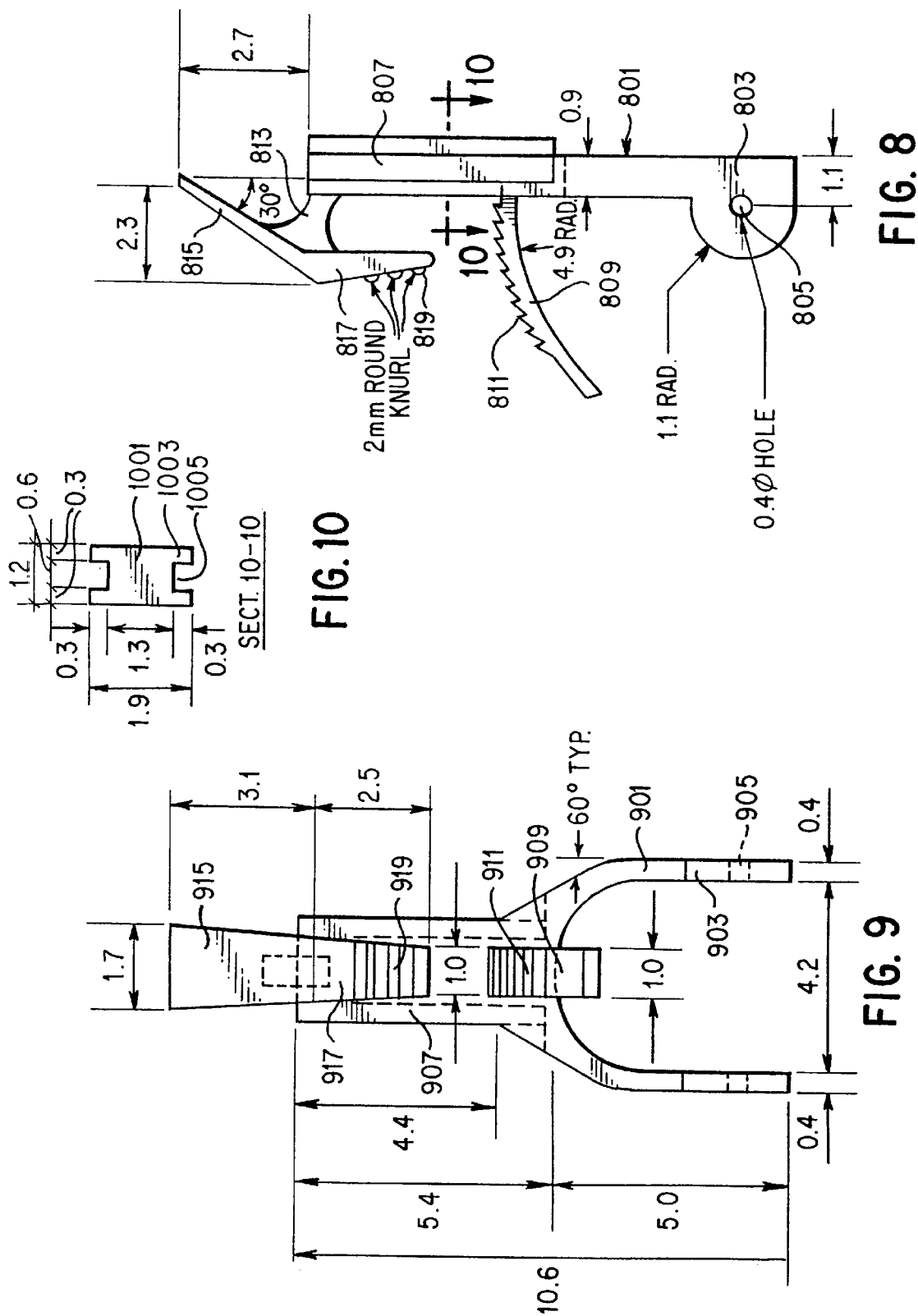

| DIM | SMALL | MEDIUM | LARGE |
|---|---|---|---|
| A | 8.1 | 10.2 | 12.7 |
| B | 3.8 | 4.7 | 5.9 |
| C | 4.7 | 5.8 | 7.3 |
| D | 5.3 | 6.6 | 8.3 |
| E | 4.6 | 5.0 | 5.7 |
| F | 3.5 | 4.3 | 5.4 |
| H | 5.4 | 6.8 | 8.5 |
| I | 6.0 | 7.4 | 9.3 |
| J | 5.4 | 6.8 | 8.5 |
| K | 5.1 | 6.4 | 8 |
| L | 7.9 | 9.9 | 12.3 |
| M | 9.0 | 11.3 | 14.1 |
| N | 2.1 | 2.2 | 2.3 |
| P | 2.9 | 3.5 | 4.3 |
| Q | 1.7 | 2.1 | 2.5 |
| R | 5.5 | 4.6 | 3.8 |
| S | 8.8 | 7.3 | 6.1 |

FIG. 11

SELF RETAINING LARYNGOSCOPE

STATEMENT REGARDING FEDERALLY SPONSORED RESEARCH OR DEVELOPMENT

Not Applicable

CROSS-REFERENCE TO RELATED APPLICATIONS

Not Applicable

BACKGROUND OF THE INVENTION

1. Field of the Invention

The present invention relates generally to medical devices and more specifically to disposable self-retaining laryngoscopes useful for orally intubating a patient with an endotracheal tube.

2. Background of the Prior Art

Laryngoscopes have long been used to open the mouth and airway to allow examination of the larynx and to assist in oral intubation of the compromised airway with an endotracheal tube.

To better understand the present invention, it is useful to review the prior art and the current state of the art in laryngoscopes. It is also necessary to understand why laryngoscope aided intubation is clinically important; why it is frequently difficult or impossible to accomplish with the prior art and to briefly discuss the consequences to the patient that can be caused by problems resulting from the use of prior art laryngoscopes.

U.S. Pat. No. 4,570,614, which issued to Bauman on Feb. 18, 1986, teaches a laryngoscope with a single disposable nonmetallic blade, a light source disposed within the handle and a light conductor disposed adjacent to and held by the blade. Typical of the prior art, this apparatus requires two hands to operate, and perhaps even two caregivers, if the patient's mouth and head must be stabilized. Lacy (U.S. Pat. No. 5,355,870) and Bar-Or et. al. (U.S. Pat. No. 5,702,351) also teach disposable plastic single blades used in combination with a light source in a laryngoscope.

U.S. Pat. No. 4,573,451, which issued to Bauman on Mar. 4, 1986, teaches a laryngoscope blade which has a tip that is capable being bent or flexed in the direction of the handle of the laryngoscope. This allows the patient's epiglottis to be lifted to expose the patient's larynx. This is a single blade instrument. It is provided with a ratchet lock to maintain the bend in the tip. This instrument can bend in only one direction, to lift the epiglottis. Locking the laryngoscope blade in an operable position is also shown in U.S. Pat. No. 5,651,760, but this lock/unlock mechanism functions to enable the instrument to be compact when it is not in use.

U.S. Pat. No. 5,036,835, which issued to Filli on Aug. 6, 1991, teaches a slideably adjustable spatula portion in the laryngoscope blade. The function of this spatula is to act as a tongue depressor to facilitate inspection of the pharynx and larynx, or the insertion of an anesthetic breathing tube. This apparatus uses a single blade with a sliding part, which does not lock in position.

U.S. Pat. No. 5,070,859, which issued to Waldvogel on Dec. 10, 1991, teaches a laryngoscope that incorporates a dynamometer in order to measure the force used by the caregiver to examine the patient. This invention is an attempt to avoid trauma to the patient that can occur using prior art apparatus.

U.S. Pat. No. 4,517,964, which issued to Upsher on May 21, 1985, teaches a dual bladed laryngoscope, wherein one conventional blade carries its own light source and the second blade is a light guide for a second light source in the handle of the instrument.

The closest prior art known to the present inventor is U.S. Pat. No. 5,498,231, which issued to Franicevic on Mar. 12, 1996. This apparatus is the current state of the art in the field of laryngoscopes. Franicevic teaches a reusable laryngoscope for use "in difficult intubation due to malformation of the jaws, tongue, pharynx, larynx or neck as a result of trauma, edema, inflammation or congenial anomalies." This laryngoscope has a hollow body terminating at its distal end in a pair of opposed blades that can be spread apart by the caregiver. An endotracheal tube slides through the hollow tube in the center of the instrument. Light conducting means are provided to illuminate the larynx. The device includes a fiberoptic optical system for inspecting the larynx during intubation. Franicevic is an improvement on the 'bendable tip' of Bauman, cited above. The single distal spreading of the 'beak' taught by Franicevic allows some lifting of the soft tissue, but it does nothing to open the mouth or depress the tongue. Franicevic teaches a bias spring to keep the distal blades closed when they are not positively spread apart by the caregiver. This apparatus is not locking or self-retaining in the airway. It also is not disposable and its complex mechanism makes it difficult to adequately sterilize.

Intubation using prior art laryngoscopes requires at least two hands. Four hands may be needed to hold the head and mouth of the patient, operate the laryngoscope and intubate the patient.

Prior art instruments are either reusable; and thus present risk of disease to the caregiver; or they use disposable single plastic blades, which become covered with blood and fail to light the airway. This can make it difficult or impossible to intubate the patient, even if the procedure is done in a hospital and the airway is normal. These problems become much more severe in the field; during emergency transportation of the patient; or when attempting to intubate an abnormal or damaged airway. When the prior art fails, effects on the patient are often severe. Respiratory related mishaps are a major source of patient morbidity and mortality. Should a difficult airway problem arise, approximately 40% will result in death, 20% in brain damage and 40% in high morbidity trauma. The incidence of difficulty in intubation is said to be between 1.2 and 2.5%, about 1 in 65 patients. This is a major medical problem, especially for the practitioner of emergency medicine. The number of different variations of laryngoscope found in the prior art is a good indication that many experts skilled in this art have tried to find solutions to these problems.

The causes of difficulty in endotracheal intubation are either congenital or acquired.

Congenital causes include conditions such as:

Pierre Robin syndrome.
Cystic hygroma.
Treacher-Collins syndrome.
Gargoylism.
Achondroplasia.
Marfan's syndrome.

Numerous anatomical features have been identified that make endotracheal intubation difficult, especially in trauma patient who must be treated promptly in the field or during transport to a hospital. These include:

excessive weight.
short muscular neck and a full set of teeth.
protruding incisors.
long high arched palate with long narrow mouth.
receding mandible.
large swellings in the neck, mouth or upper chest.
decreased distance between the occiput and the spinous process of C.1.
increase in posterior depth of the mandible.
increase in alveolar—mental distance requiring wide opening of the mandible.

Endotracheal intubation using prior art laryngoscopes may also be difficult or impossible because of acute swelling in the neck due to trauma or bleeding. Intubation may be difficult if flexion of the neck is contraindicated because of cervical spine injury or severe rheumatoid arthritis.

The following categories of patients require a definitively secured airway:

1. Apnoea
2. <9 or sustained seizure activity.
3. Unstable mid-face trauma.
4. Airway injuries.
5. Large flail segment or respiratory failure.
6. High aspiration risk.
7. Inability to otherwise maintain an airway or oxygenation.

The urgency of airway intubation is the most important factor in planning which technique of securing the airway is the safest and most appropriate. The caregiver must evaluate and assess the risk of further cord injury given head and neck movement, the degree of cooperation from the patient, anatomy and trauma to the airway and the caregiver's own expertise in each technique. Initially the airway should be cleared of debris, blood and secretions. It should be opened using the 'chin lift' or 'jaw thrust' maneuvers. The 'sniffing the morning air' position for standard tracheal intubation flexes the lower cervical spine and extends the occiput on the atlas. An oral (Guedel) or nasopharyngeal airway may be necessary to maintain patency until a definitive airway is secured. Insertion of an airway produces minimal disturbance to the cervical spine. Bag and mask ventilation also produces a significant degree of movement at zones of instability.

The ATLS recommends a nasotracheal tube in the spontaneously breathing patient, and orotracheal intubation in the apnoeic patient. MANUAL in-line axial stabilization must be maintained throughout. The hard collar may interfere with intubation efforts and the front part may be removed to facilitate intubation as long as manual stabilization is in effect. Blind nasal intubation is successful in 90% of patients but requires multiple attempts in up to 90% of these. Nasotracheal intubation is (relatively) contraindicated in patients with potential basillar skull fracture or unstable mid-face injuries. In addition, it may produce hemorrhage in the airway, making other airway manipulations difficult or impossible.

Orotracheal intubation is generally accepted as the more usual method for securing the airway in the trauma patient. It is the fastest and surest method of intubating the trachea. At Shock Trauma in Baltimore, Md. (Grande C. M., Barton C. R., Stene J. K. "Appropriate Techniques for Airway Management of Emergency Patients with Suspected Spinal Cord Injury." Anesth Analg 1988;67:714–715) more than 3000 patients were intubated orally with a modified rapid sequence induction technique with pre-oxygenation and cricoid pressure. Ten percent of these patients were found to have cervical spine injury and none deteriorated neurologically following intubation.

Awake intubation is also a feasible option and is favored by some practitioners. It may be performed via the nasotracheal route, direct oral laryngoscopy or by fibreoptic technique. Successful fibreoptic tracheal intubation requires a cooperative patient, a secretion and blood free airway, a pharynx unrestricted by oedema and adequate supraglottic and infraglottic anesthesia. Such ideal conditions often do not exist, and local anaesthetic preparation of the airway is time consuming and might increase the risk of aspiration even if done in a proper hospital. Failed or difficult intubation is always a problem. Some nontramatic causes are:

A. difficult blade insertion in the obese patient
B. absence of any landmarks
C. ineffective lighting
D. inability to pass endotracheal tube Complications of direct laryngoscopy and intubation as taught by the prior art can be severe and can include:

A. hypoxia
B. esophageal intubation
C. glottic and epiglottic edema
D. vocal cord injury
E. tracheal perforation
F. dental trauma
G. endobronchial intubation
H. pulmonary aspiration
I. laryngospasm
J. bronchospasm
K. cervical spine injury
L. increased intracranial pressure
M. increased intraoculary pressure
N. pulmonary edema In addition to these risks to the patient, most prior art laryngoscopes are reused. This is always true of complex designs, such as the laryngoscope taught by Franicevic, cited above. Such prior art laryngoscopes can present a risk of disease to the caregiver because they are often not possible to completely sterilize them after use. In most cases they are even not sterilized, but just washed by hand.

BRIEF SUMMARY OF THE INVENTION

The invention is a self-retaining disposable laryngoscope having dual light conductive blades that open and lock apart laterally and/or radially. The invention has two curved blades: a tongue blade and a palate blade. These two blades may be separated and locked apart by a ratchet mechanism in the instrument's handle while they remain parallel. This provides a bite block, pushes down the tongue, and makes the invention self-retaining in the airway. The palate blade may be rotated about an axis in the handle of the instrument and locked in position by a ratchet mechanism to spread the distal ends of the blades. This lifts the tongue and epiglottis and opens the airway. Both plastic blades are light conductors for a source of light located in the handle. Light from both blades assures that one blade being covered with blood will not prevent adequate light from illuminating the airway. The present invention may be operated with one hand initially and then locked, freeing both hands because the blades lock into position in the airway when they are separated and/or rotated.

It is therefore a principle object of the present invention to provide a dual blade laryngoscope whose blades can lock open both laterally and radially to allow endotracheal intubation of the difficult airway.

A further object of the present invention is to provide a laryngoscope capable of simultaneously opening the mouth, lifting the tongue and lifting the epiglottis, whereby it is self-retaining in the airway.

Another object of the present invention is to provide a laryngoscope that adequately lights the airway during intubation even if one blade of the instrument is obscured by blood or foreign material.

A further object of the present invention is to provide a laryngoscope that provides a bite block to prevent dental trauma, and to protect integrity of the airway and personnel.

Yet a further object of the present invention is to provide a laryngoscope that is inexpensive and disposable.

An important object of the present invention is to provide a laryngoscope that may be operated with one hand and by caregivers not trained as experts at endotracheal intubation

BRIEF DESCRIPTION OF THE SEVERAL VIEWS OF THE DRAWINGS

FIG. 2 is a side view of the palate blade of the present invention;

FIG. 3 is a top view of the palate blade of the present invention;

FIG. 8 is a side view of the slide/rotary ratchet mechanism of the present invention;

FIG. 9 is a rear view of the slide/rotary ratchet mechanism of the present invention;

FIG. 10 is a section view taken along section lines 10—10 of FIG. 8; and

FIG. 11 is a table showing typical dimensions of the drawings shown in FIGS. 1–10 for small, medium and large laryngoscopes.

DETAILED DESCRIPTION OF THE INVENTION

FIGS. 1 to FIG. 10, inclusive, show preferred angles and dimensions of the best embodiment of the present invention known to the inventor. In some cases distances are marked with letters of the alphabet rather than numeric values. This is done because laryngoscopes must be made in several sizes, for children and adults, as well as to take into account the normal size variations in patients. The values for these dimensions are given in the table shown in FIG. 11. It is the intention of the inventor to thereby give a sufficient disclosure of the present invention to allow any person skilled in the art of making laryngoscopes the ability to make and use the present invention without undue experimentation.

Figure 1:
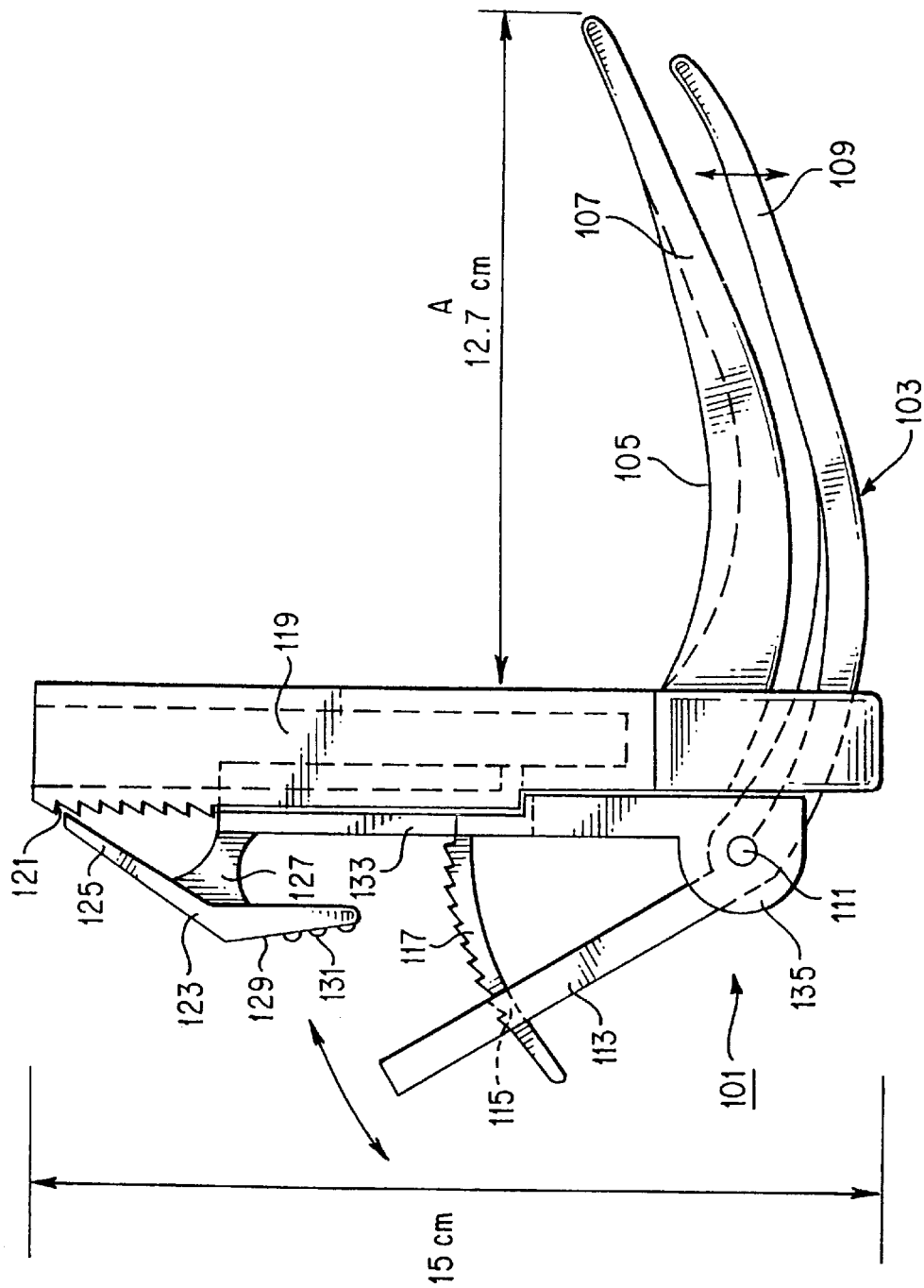
FIG. 1 shows a side view of the present invention.

FIG. 1 shows a side view of the preferred embodiment of the present invention. Structurally, In FIG. 1, laryngoscope 101 has a curved palate blade 103 having a palate blade tip 109. Laryngoscope 101 also has a tongue blade 105 having a tongue blade tip 107. Blades 103 and 105 are curved in a manner well known to those skilled in the art and are roughly parallel to each other.

Palate blade 103 has a rotation axis 111 and a lever portion 113. Lever portion 113 is adapted to operable receive ratchet member 115 of ratchet mechanism 117. Ratchet mechanism 117 is part of lateral/radial ratchet assembly 133. The lower part 135 of assembly 133 has a hole for receiving axis 111.

Tongue blade 105 has an upright portion 119 that has a ratchet mechanism 121. Ratchet 121 engages tip 125 of rocker lever 123. Lever 123 is attached to assembly 133 by semi-rigid shaft 127. Lever 123 has a lower part 129 that is equipped with finger knurls 131.

A battery, switch and light source, not shown, are disposed within upright member 119.

Blades 103 and 105 are made by injection molding of any plastic that is suitable for medical devices and capable of conducting light along the length of the blades. Assembly 133 is made by injection molding from any plastic suitable for medical use that is strong and resilient enough to allow the ratchet mechanisms to operate reliably.

Functionally, laryngoscope 101 operates as follows. The patient's head is stabilized. The mouth is opened. Blades 103 and 105 are proximate each other and are placed into the airway. With the thumb of the one hand holding the laryngoscope, the caregiver pushes rocker lever 123 and slides palate blade 103 away from tongue blade 105. As this is done, the end 125 of lever 123 engages ratchet 121 of the upright part 119 of blade 105. The result is that blades 103 and 105 separate and lock apart while remaining in parallel. This depresses the tongue and elevates the palate. The patient's mouth is opened wide and locked open by the laryngoscope, which also acts as a bite block. The patient's airway is illuminated by light from both blades of the invention. Natural tension of the patient's jaw and mouth makes the invention self-retaining in the patient's airway. It remains in place without requiring either the hands or attention of the caregiver until lever 129 is pressed, which releases lever 125 from ratchet mechanism 121 and allows blades 103 to return to its original position adjacent to blade 105.

When laryngoscope 101 has its two blades 103 and 105 laterally separated and locked by the ratchet mechanism of the invention in the patient's airway, the entire attention of the caregiver can be directed to the work of intubation. If necessary, the caregiver may press lever section 113 of palate blade 103 towards the handle of the invention using the thumb of the hand holding the laryngoscope. When lever section 133 is moved toward assembly 113, it rotates palate blade 103 about axis 111 and causes palate blade tip 109 to separate at its distal end from the tip 107 of tongue blade 105. As this happens, ratchet member 115 of lever 113 engages ratchet mechanism 117 of assembly 133 to lock the blade tips apart. This action at the blade tips lifts the soft tissue and exposes the larynx. When this is accomplished, the caregiver may leave the invention locked in position and concentrate entirely on intubating the patient. Blade tips 107 and 109 will remained locked in the open position until the end of ratchet mechanism 118 is depressed allowing palate blade 103 to return to its original position.

FIG. 2 shows a side view of the palate blade of the preferred embodiment of the present invention. In FIG. 2, palate blade 201 has a projecting axis 202, a palate portion 211 having curved end sections 213 and 215. Opposite axis 202 from end 215, is lever 203 having a ratchet engagement part 205 with a ratchet engagement tooth 207. The angles and distances shown on in FIG. 2 refer to the table in FIG. 11.

FIG. 3 shows a top view of the palate blade of the preferred embodiment of the present invention. In FIG. 3 the palate blade's palate section 311 is shown with ends 313 and 315 and palate blade tip 309. Opposite axis 302 from section 311, lever section 303 is shown with opening 304. Opening 304 accommodates the upright section of the tongue blade and the lateral and radial ratchet assembly, described in connection with FIG. 1 above. The angles and distances shown in FIG. 3 are referenced to the table of sizes disclosed in FIG. 11.

Figure 4:
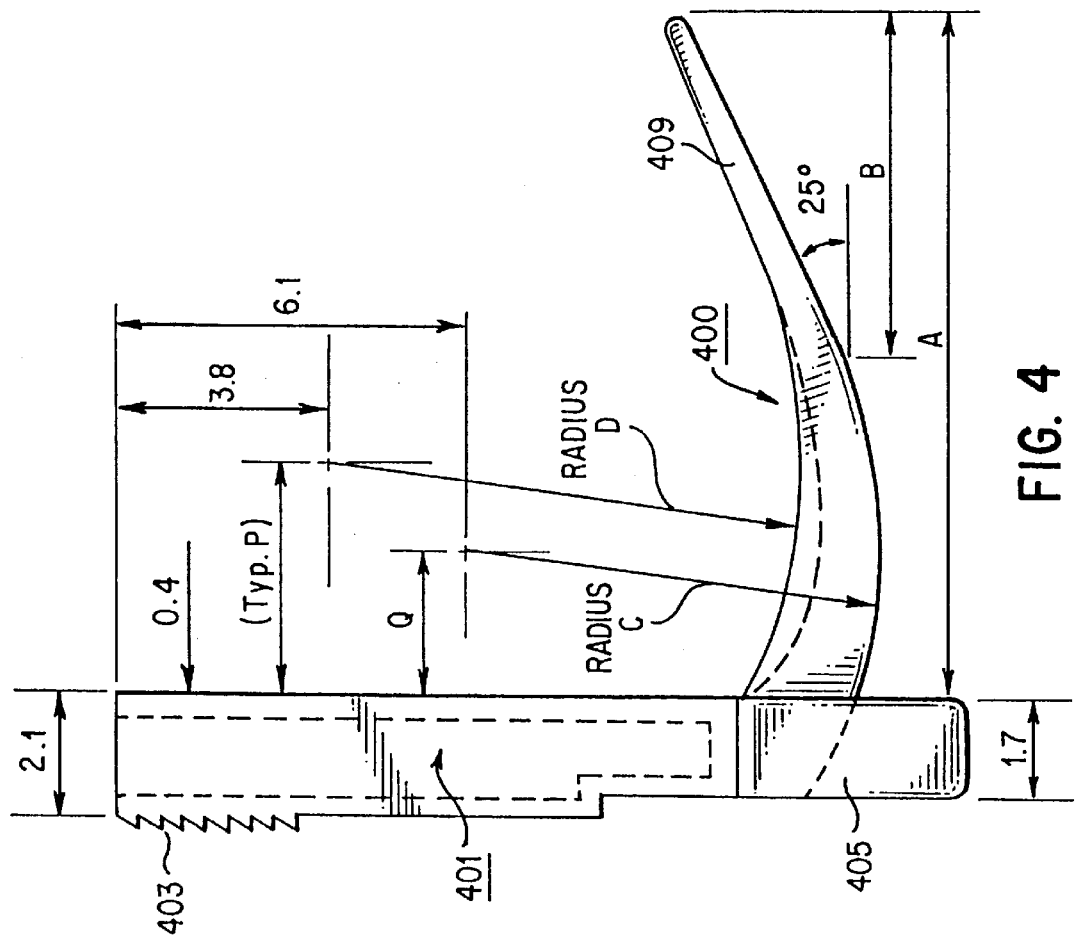
FIG. 4 is a side view of the tongue blade of the present invention.

FIG. 4 shows a side view of the tongue blade of the preferred embodiment of the present invention. In FIG. 4, tongue blade assembly 400 has a curved transparent tongue blade having a tongue blade tip 409. Blade assembly 400 also has an upright section 401 having a base member 405 and a ratchet assembly 403 on its side opposite blade. The distances and angles shown in FIG. 4 refer to the table in FIG. 11. Inside the upright portion 401 of tongue blade assembly 400 is a light source, not shown, for illuminating the transparent light conducting blades of the present invention.

Figure 5:
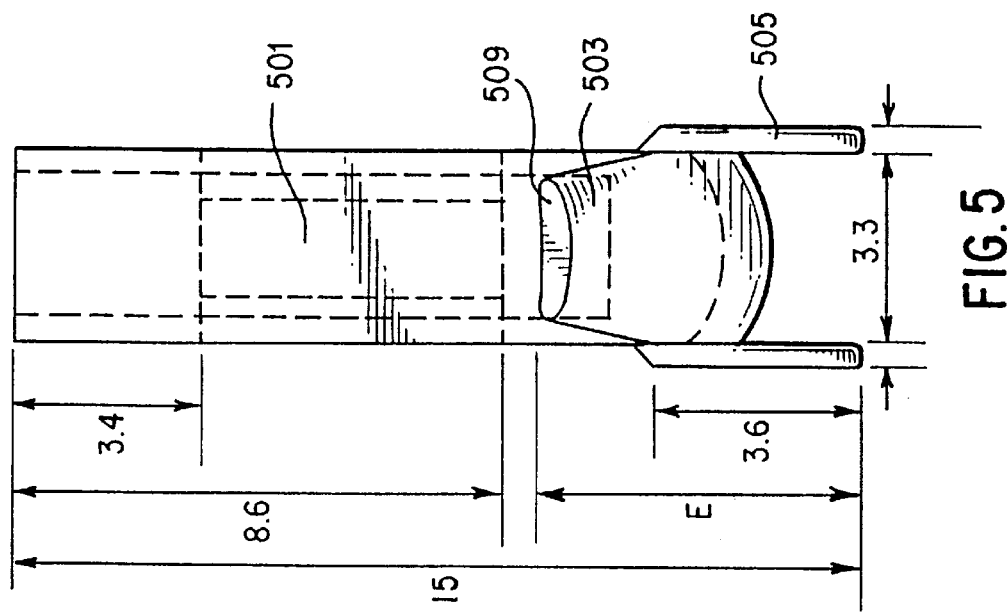
FIG. 5 is a front view of the tongue blade of the present invention.

FIG. 5 is a front view of the tongue blade assembly of the preferred embodiment of the present invention. In FIG. 5, upright section 501 is shown in relation to the curved portion of blade 503, which has an end 509. The lower portion 505 of the assembly is also shown. The sizes and distances shown in FIG. 5 refer to the table in FIG. 11.

Figure 6:
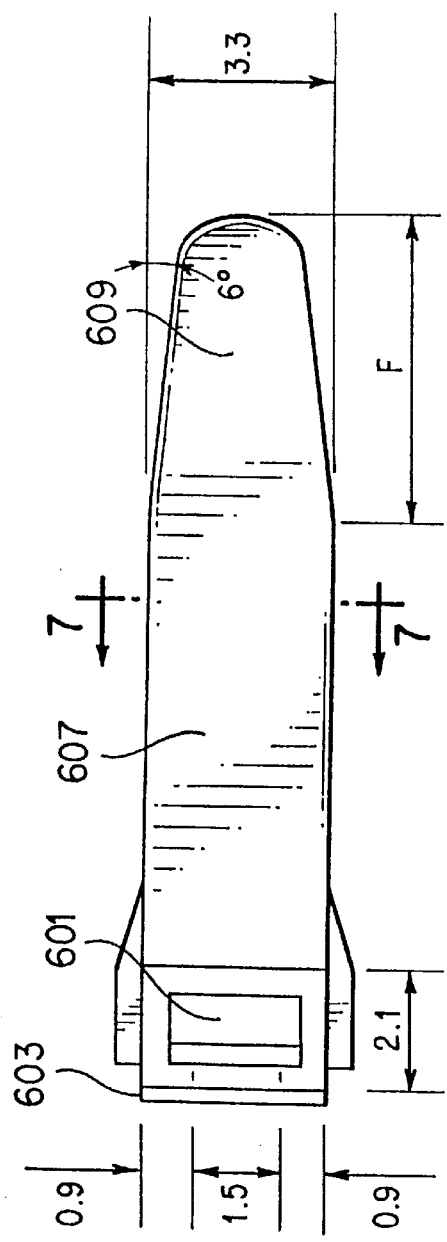
FIG. 6 is a top view of the tongue blade of the present invention.

FIG. 6 is a top view of the tongue blade of the preferred embodiment of the present invention. In FIG. 6, upright section 601 is shown attached to blade 607, which has a tapered tip section 609. Ratchet mechanism 603 is shown on the side of blade upright section 601 that is opposite blade section 607.

Figure 7:
FIG. 7 is a section view of the tongue blade taken along section lines 7—7 of FIG. 6.

FIG. 7 is a cross section of the tongue blade of the preferred embodiment of the present invention taken along section lines 7—7 of FIG. 6. FIG. 7 is presented to show the curvature of the tongue blade.

FIG. 8 is a side view of the slide/rotary ratchet mechanism of the present invention. In FIG. 8, mechanism 801 has a lower rounded portion 803 having a hole 805. Mechanism 801 also has an upper engaging porting 807. Simi-rigid member 813 mounts lateral ratchet lever 815 to engaging portion 807. Lever 815 has a release end 817 having knurls 819. About the middle of mechanism 801 is a curved projecting member 809 having a ratchet mechanism 811 on its upper side. This is the most complex molded part of the present invention. Care must be taken to ensure that the structural elements used for engaging the ratchet locks for the lateral and radial separation of the blades of the present invention have the proper degree of flexibility.

FIG. 9 is a rear view of the slide/rotary ratchet mechanism of the present invention. In FIG. 9 equivalent numbers beginning with '9' indicate equivalent structures to FIG. 8's numbers beginning with '8'.

FIG. 10 is a cross section view taken along section lines 10—10 on the engaging section 808 of FIG. 8. In FIG. 10, engaging section 1001 has projections 1003 that define a channel 1005. A similar channel is defined on the opposite side of the section.

FIG. 11 is a table showing the dimensions of the proffered embodiment of the present invention for small, medium and large versions of the invention.

In this detailed specification the inventor has disclosed in the best embodiment of his invention known to him at the time he made application for letters patent. Many variations of size, shape and details of structure could be made by persons skilled in the art of making medical devices that would still be this invention. For example, the ratchet locking mechanism shown in this specification could be replaced by a set of screw threads or a friction locking mechanism to hold the blades in their proper position. This detailed embodiment of the present invention should therefore be read and understood as illustrating, but not limiting, the scope of my invention. The invention should be limited only by the following claims.

I claim:

1. A laryngoscope comprising:

an elongated body, a tongue blade having a proximal end attached to said body and a distal end, a palate blade having a proximal and a distal end, said palate blade being substantially parallel and proximate said tongue blade, said tongue and palate blades being curved congruently with respect to one another, lateral separation means fixed to the proximal end of at least one of said blades and to said body for moving said blades apart while holding them substantially parallel, lateral locking means for releasably locking said blades in a spaced apart position, radial separation means fixed to the proximal end of at least one said blade for radially separating the distal ends of said blades, and radial locking means for releasable locking said blades in a fixed position when their distal ends are separated.

2. A laryngoscope as in claim 1 wherein the lateral separation means comprises a slide adapted to move on said body, said lateral locking means comprises a ratchet mechanism said radial separation means comprises an axis of rotation fixed to said palate blade and said radial locking means comprises a ratchet mechanism.

3. A laryngoscope comprising, a curved palate blade connected to a base, a curved tongue blade connected to a base, said tongue and palate blades being curved congruently with respect to one another, said blades are light conductors, the palate blade base slidably connected to the tongue blade base and held by a first ratchet mechanism.

4. The laryngoscope of claim 3, wherein the palate blade is pivotably connected to the palate blade base.

5. The laryngoscope of claim 4, further comprising a lever connected to the palate blade and extending from said palate blade base.

6. The laryngoscope of claim 5, further comprising a second rachet extending from the palate blade base and engaging the lever.

7. The laryngoscope of claim 3, wherein the first ratchet mechanism comprises ratchet teeth on the tongue blade base and a pawl connected to the palate blade base.

8. The laryngoscope of claim 7, wherein the pawl is connected to the palate blade base by a shaft, and a release lever connected to the pawl.

9. The laryngoscope of claim 3, wherein the palate blade and tongue blade are transparent.

10. The laryngoscope of claim 3, further comprising a light source in the tongue blade base.

* * * * *